United States Patent [19]
Brenneisen et al.

[11] 3,933,841
[45] Jan. 20, 1976

[54] 2-PHENOXY, -PHENYLTHIO-, AND -PHENYL-AMINO-BENZOXAZOLES HAVING AN ISOTHIOCYANO SUBSTITUENT

[75] Inventors: Paul Brenneisen, Basel; Thomas Wenger, Riehen; Jean-Jacques Gallay, Magden, Aargau; Wolfgang Schmid, Neuallschwil, all of Switzerland

[73] Assignee: Ciba-Geigy Corporation, Ardsley, N.Y.

[22] Filed: July 24, 1974

[21] Appl. No.: 491,584

Related U.S. Application Data

[62] Division of Ser. No. 255,334, May 22, 1972, Pat. No. 3,840,550.

[30] Foreign Application Priority Data

May 24, 1971 Switzerland............ 7542/71

[52] U.S. Cl............................ 260/307 D; 260/309.2
[51] Int. Cl.[2].............................. C07D 263/58
[58] Field of Search................... 260/307 D

[56] References Cited
UNITED STATES PATENTS

3,586,670  6/1971  Brenneisen et al............... 260/240
3,840,550  10/1974  Brenneisen et al............... 260/304
3,849,431  11/1974  Gallay et al................... 260/306.6 R

*Primary Examiner*—Raymond V. Rush
*Attorney, Agent, or Firm*—Frederick H. Rabin

[57] ABSTRACT

Isothiocyano substituted 2-phenoxy, 2-phenylthio and 2-phenylamino-benzoxazoles have anthelmintic activity in warm-blooded animals. Included are compounds of the formula

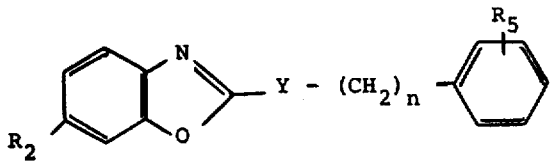

in which one of $R_2$ and $R_5$ is isothiocyano and the other is hydrogen, methyl, methoxy, chlorine or nitro; Y is oxygen, sulphur or

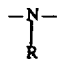

wherein R is hydrogen or methyl; and $n$ is 0 or 1.

3 Claims, No Drawings

2-PHENOXY, -PHENYLTHIO-, AND -PHENYL-AMINO-BENZOXAZOLES HAVING AN ISOTHIOCYANO SUBSTITUENT

This is a division of application Serial No. 255,334, filed on May 22, 1972, now U.S. Pat. No. 3,840,550.

The present invention relates to new isothiocyanobenzazoles, to processes for their production, as well as to anthelmintic agents containing these new isothiocyanobenzazoles as active substance.

Among the endoparasites to be found in warm-blooded animals, the helminthes, in particular, are ones causing a great deal of harm. Thus, for example, the infestation of animals by worms leads not only to a retardation in growth, but also to the frequent occurrence of damage so severe that it can result in the death of the affected animals. It is therefore of the greatest importance that agents be developed which are suitable for the control of helminthes and of their development stages, as well as for the prevention of infestion by these parasites. A number of substances having anthelmintic action have become known; but frequently these are not able, however, to fully satisfy the requirements: either they have an inadequate effect in compatible doses with undesirable side-effects, however, in the case of therapeutically effective doses, or they possess too narrow a range of action. For example, d,1-2,3,5,6-tetrahydro-6-phenyl-imidazo-[2,1-5]thiazole, known from the Dutch Pat. No. 6,505,806, is effective only against nematodes, but not against trematodes and cestodes. In addition, isothiocyanobenzazole derivatives having anthelminthic activity are known from the Belgian Pat. No. 599,143.

In the present description the term 'helminthes' applies to nematodes, cestodes and trematodes; in particular, therefore, to worms of the gastrointestinal tract, of the liver and of other organs.

The new anthelmintically effective isothiocyanobenzazoles coresspond to the general formula I:

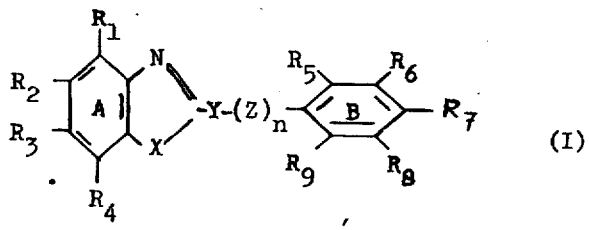

wherein each of the substituents $R_1$ to $R_4$ and/or each of the substituents $R_5$ to $R_9$ represent the isothiocyano group, and the remaining substituents of the benzene nucleus A independently represent hydrogen, halogen, nitro, hydroxy, alkyl, alkoxy, halogenalkyl, and those of the benzene nucleus B each independently represent hydrogen, halogen, nitro, cyano, alkyl, alkoxy, halogenalkyl, alkylamino, dialkylamino, alkanoylamino, phenyl, or two substituents in the ortho-position with respect to each other represent a benzene nucleus bound to the nucleus B, X represents oxygen, sulphur, or the group $>N-R$ wherein R represents hydrogen, alkyl, alkenyl, alkanolyl, alkyl substituted by benzoyl or halogenated benzoyl, benzene optionally substituted by halogen, or phenyl or benzyl optionally substituted by alkyl, Y represents oxygen, sulphur, or the group $>N-R'$ wherein $R'$ represents hydrogen, alkyl or alkenyl, Z represents a straight-chain or branched alkylene bridge member, and n represents the number 0 or 1, with the proviso that, among the radicals $R_1$ to $R_9$, the isothiocyano groups are, in each case, only in the m- or p-position to hydroxy or alkylamino groups, and that, if Y represents the NH— group and n equals 0, the substituents $R_5$ and $R_9$ do not represent isothiocyano, as well as their addition salts and quaternary salts non-toxic in anthelmintically effective doses for the organism of warm-blooded animals.

Y is preferably oxygen, sulphur, the group $>NH$ or $>N-CH_3$.

The aliphatic bridge-member Z is preferably ethylene or vinylene.

The above mentioned substituents R and R' of the groups $>N-R$ and $>N-R'$, respectively, represents in preferred compounds of the general formula I: hydrogen or alkyl.

The alkyl radicals mentioned in the above definition of the substituents of the general formula I preferably contain 1 to 4 carbon atoms; the correspondingly defined alkenyl radicals preferably 3 or 4 carbon atoms.

Suitable non-toxic salts of compounds of the general formula I are preferably the acid addition salts non-toxic in anthelmintically effective doses for the organism of warm-blooded animals.

By addition salts are preferably meant the salts of the following inorganic and organic acids: hydrohalic acids such as hydrochloric acid, hydrobromic acid, phosphoric acid, sulphuric acid, fluoboric acid ($HBF_4$), perchloric acid, alkylsulphuric acid such as methyl- or ethyl-sulphuric acid, naphthoic acids, benzoic acid, halogenobenzoic acids, acetic acid, halogenoacetic acids such as trichloroacetic acid, aminoacetic acid, propionic acid, halogenopropionic acids, butyric acid, lactic acid, stearic acid, aliphatic dicarboxylic acids such as oxalic acid, tartaric acid, maleic acid, aromatic sulphonic acids such as p-toluenesulphonic acid, etc. Such inorganic and organic acids are likewise suitable for the formation of quaternary salts of the pyrimidine derivatives of formula I wherein $R_1$ and/or $R_3$ represent a trialkylammonioalkyl radical.

The new isothiocyanobenzazoles of formula I are produced according to the invention by the reaction of an aminobenzazole of formula II:

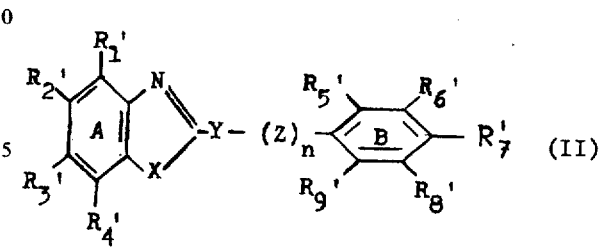

wherein each one of the substituents $R_1'$ to $R_4'$ and/or each one of the substituents $R_5'$ to $R_9'$ represent(s) the amino group, and the remaining substituents of the benzene nucleus A each independently represent hydrogen, halogen, nitro, hydroxy, alkyl, alkoxy, halogenalkyl, and those of the benzene nucleus B each independently represent hydrogen, halogen, nitro, cyano, alkyl, alkoxy, halogenalkyl, alkylamino, dialkylamino, alkanoylamino, or phenyl, or two substituents in the ortho-position with respect to each other represent a benzene nucleus bound to the nucleus B, and the symbols X, Y, Z and n have the meanings given under formula I, with the proviso that, among the radicals $R_1'$ to $R_9'$, the amino groups are, in each case, only in the m- or p-position with respect to hydroxy- or alkylamino groups, and that, if Y denotes the NH—group and n equals 0, the substituents $R_5'$ and $R_9'$ do not represent amino, the said reaction being performed with a reagent capable of converting the amino groups into isothiocyanato groups, preferably in the presence of a solvent or diluent inert to the reactants.

Suitable reagents capable of introducing a thiocarbonyl group in the process according to the invention are given below:

a. a thiocarbonic acid derivative of the general formula II:

wherein Hal represents chlorine or bromine, and

Y represents chlorine, bromine, or a dialkylamino group, and by which definition is preferably meant thiophosgene, which is optionally reacted in the presence of an acid-binding agent at temperatures of between 0° and 75°, and N,N-diethylthiocarbamoyl chloride, which is reacted at temperatures of between 40° and 200°;

b. a bis-thiocarbamoylsulphide of the general formula III;

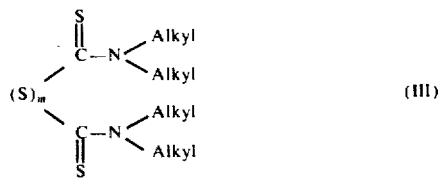

wherein the index m represents the number 1 or 2, and alkyl preferably denotes ethyl, in the presence of hydrogen halide;

c. pentathio-dipercarbonic acid-bis-trichloromethyl ester;

d. ammonium rhodanide in the presence of gaseous HCl;

e. phosgene and phosphorus pentasulphide;

f. carbon disulphide in the presence of an inorganic or organic base; the amino group is firstly converted into the dithiocarbamic acid salt, which is then dehydrosulphated to the isothiocyano group;

g. ammonium rhodanide and benzoyl chloride, and thermal decomposition of the intermediate thiourea to the isothiocyano derivative;

h. carbon disulphide and dicyclohexylcarbodiimide in the presence of a tertiary amine.

i. The new isothiocyanobenzazoles of formula I can also be obtained by a process in which, instead of amine, a corresponding nitro, nitroso, azo or azoxy compound is reacted under pressure.

1. with carbon disulphide, carbon oxysulphide, or mixtures of carbon disulphide and carbon oxysulphide, in the presence of potassium hydrogen sulphide, with tetraalkylurea as the solvent (cp. German Offenlegungsschrift No. 1,954,483); or 2. with carbon oxysulphide in the presence of potassium fluoride and a solvent (aliphatic, aromatic, cycloaliphatic hydrocarbon), likewise under pressure (cp. German 'Offenlegungsschrift' No. 1,954,484).

The reaction with thiophosgene is performed, for example, according to Houben-Weyl, 4th edition, Vol. 9, p. 867 onward (1955); and with employment of acid-binding agents according to O.E. Schultz in Arch. Pharm. 295, 146 – 151 (1962); the reaction with N,N-diethylthiocarbamoyl chloride is carried out according to org. Chem. 30, 2465 (1965); that with bis-thiocarbamoylsulphides according to F.H. Marquardt, Helv. Chim. Acta, 49, 1716 (1966), that with pentathiodipercarbonic acid-bistrichloromethyl ester according to R. Gottfried, 'Angew. Chem.' (Applied Chem.) 78,985 (1966), that with ammonium rhodanide and HCl gas according to the British Pat. No. 1,099,768, and the reaction with phosgene and phosphorus pentasulphide according to Houben-Weyl, 4th Edition, Vol. 9, p. 867 onward. The dehydrosulphation following the reaction with carbon disulphide and bases can be performed oxidatively with metal salts (British Pat. No. 793,802, Dutch Pat. No. 81,326); it can be performed, e.g. with lead-, copper-, zinc- or iron-III-salts, iodine, alkali metal hypochlorites or -chlorites, preferably with sodium and potassium salts (French Pat. No. 1,311,855), also with suitable acid halides such as with 78, 985 and phosphorus oxychloride [D. Martin et al., Chem. Ber. 98, 2425–2426 (1965)], as well as with $Cl_2$ and ammonium sulphide (German 'Auslegeschrift' No. 1,192,189), or chloroamine T (British Pat. No. 1,024,913).

The reaction with ammonium rhodanide and benzoyl chloride, which firstly leads to the thiourea derivative which is converted by heating, e.g. in boiling chlorobenzene, into the isothiocyano derivative, is performed, for example, according to Houben-Weyl, 4th Edition, Vol. 9, page 867 onward; and the reaction with carbon disulphide and dicyclohexylcarbodiimide, in the presence of a tertiary amine, is carried out according to J.C. Jochims, Chem. Ber. 101, 1746 (1968).

Examples of inert solvents or diluents which can be used in the process according to the invention are as follows:

aliphatic and aromatic hydrocarbons,
aliphatic and aromatic halogenated hydrocarbons,
ethers and ethereal compounds, ketones, amides such as
dimethylformamide, etc., water, or mixtures of such solvents with water.

The benzazole compounds embraced by formula II wherein X stands for the group >NH can be converted by reaction with conventional acylating, alkylating or alkenylating agents into the corresponding derivatives.

The amines serving as starting materials may be used in the form of the free bases, and also as addition salts with acids, particularly with mineral acids.

The aminobenzazoles embraced by formula II and serving as starting materials are, in some cases, described in the literature; or they can be produced by known processes, e.g. by catalytic hydrogenation, or by the Bechamp reduction of the corresponding nitro compounds which can be obtained, amongst other means, by nitration of suitable benzazoles (cp. Houben-Weyl-Muller, Methods of Organic Chemistry, Vol. XI/1, 1957).

The production of such nitrobenzazoles is generally known. Nitrosubstituted 2-anilinobenzimidazoles can be obtained, for example, by the reaction of phenyl- or p-chlorophenylcarbonimidoyl-dichloride with o-phenylenediamines substituted by nitro groups (cp. J. org. Chem. 29, 1613-1615, 1964). 5.4'-Dinitro-1- anilinobenzothiazole can be produced from s-di-p-nitrophenylthiocarbamide with ring formation by the action of bromine, and a subsequent reducing treatment (see J. Chem. Soc. 1929, 464. Suitable benzazoles, which are substituted on the aromatic nuclei with sulphonamide groups, can also be subjected to hydrolysis, whereby the correspondingg aminobenzazoles are obtained. Furthermore, various processes have already been described for the production of the aminobenzazoles to be used as starting materials in the process according to the invention in which processes the starting compounds are 2-halogen-benzazoles; these are reacted with suitably substituted phenols, thiophenols or anilines to give the corresponding 2-phenoxybenzazoles (cp. French Pat. No. 1,242,962, Chemical Abstracts 55, 21928a), phenylthiobenzazoles (Cp. J. Chem. Soc. (B) 1968, 1280–1284), or anilinobenzazoles (Ann. Chimica 44, 3–10, 1954; Helv. Chim. Acta 44, 1273–1282, 1961). Compounds of the type 1-aminoalkyl-2-anilinobenzimidazoles can be produced by the ring-closure reaction of 2-(alkyl-aminoalkylamino)anilines with S-methylisothioureas (cp. U.S. Pat. No. 3,000,898).

According to a type of reaction not hitherto described, substituted benzimidazoles corresponding to formula II can be obtained which, according to the invention, can be used as starting materials for the present invention. For this purpose, a suitably substituted 2-halogenbenzimidazole of the formula:

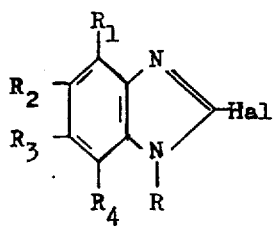

wherein the radicals $R_1$ to $R_4$ each independently represent hydrogen, halogen, nitro, hydroxy, amino, alkyl, alkoxy, or halogenalkyl, and the radical R represents hydrogen, alkyl, alkenyl, alkanoyl, alkyl substituted by benzoyl or halogenated benzoyl, benzoyl optionally substituted by halogen, or phenyl or benzyl optionally substituted by alkyl, and Hal denotes halogen, preferably chlorine, is reacted with an aminophenol of the formula:

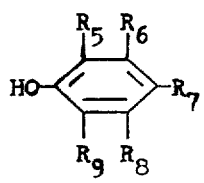

wherein the radicals $R_5$ to $R_9$ each independently represent hydrogen, halogen, nitro, cyano, alkyl, alkoxy, halogenalkyl, amino, alkylamino, dialkylamino, alkanoylamino, phenyl, or two substiuents in the ortho-position with respect to each other represent a bound benzene nucleus, and the amino group is preferably in the m- or p-position with respect to the hydroxy group. The reaction is performed in the presence of a stong base (KOH, NaOH), preferably in an equimolar amount with respect to the benzimidazole. On the other hand, the aminophenol is present in excess, preferably in an excess of 2 moles per mole of benzimidazole. The reaction is performed at 140°–145°C, with separation by distillation of the formed water. The product essentially obtained with o-aminophenol is 2-(1'-hydroxyanilino)-benzimidazoles.

On account of their excellent anthelmintic activity, the new isothiocyanobenzazoles of the following formula III:

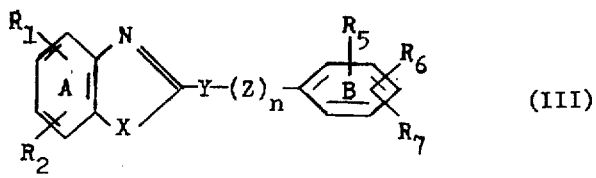

wherein the radicals $R_1$, $R_2$, $R_5$, $R_6$ and $R_7$, as well as the symbols Y, Z and n, have the meanings given under formula I, with account being taken of the defined exceptions, whereby the isothiocyano group in the nucleus A is in the 5- or 6-position, and/or that in the nucleus B in the 2'(o)-, 3'(m)- or 4'(p)-position with respect to the bridge member, are of particular importance.

The benzazole compounds according to the invention and their salts display a pronounced anthelmintic action against the most important nematodes infesting animals and human beings (e.g. ascaridae, trichostronglidae, ancylostomatidae, strongylidae), cestodes (e.g. anoplocephalidae, taeniidae) and trematodes (e.g. fasciolidae, schistosomidae). The control of helminthes is of special significance in the case of domestic animals and productive livestock, such as, e.g. cattle, pigs, horses, sheep, goats, dogs, cats, as well as poultry. The active substances according to the invention can be administered to the mentioned animals either as single doses or as repeated doses. A better effect is obtained in some cases by a protracted administration of the active substances, or it is possible, in other cases, to obtain the desired effect with smaller overall doses. The active substances, or mixtures containing them, may also be added to the feed or to the water, the active substance concentrations then being between 0.01 and 1%.

The new active substances can be administered to the animals direct, orally or abomasally, in the form of solutions, emulsions, suspensions (drenches), powders, tablets, boluses and capsules, the administration being either in the form of a single dose or in the form of repeated doses. In some cases, a better effect is achieved by a protracted administration, or a lesser amount as an overall dose may suffice. The active substances, or mixtures containing them, can also be added to the feed or to the water, or they may be contained in so-called feed premixtures.

The usual carriers are used for the preparation of the dosage units, such as kaolin, talcum, bentonite, sodium chloride, calcium phosphate, carbohydrates, cellulose powders, cottonseed meal, carbowaxes, gelatine, or liquids such as water, optionally with the addition of surface-active substances such as ionic or non-ionic dispersing agents, as well as oils and other solvents harmless to the organism of animals. If the anthelmintic agents are in the form of feed concentrates, then suitable carriers are, e.g. productive feeds, fodder grain or protein concentrates. Such feed concentrates may contain, in addition to the active substances, additives, vitamines, antibiotics, chemotherapeutics, bacteriostatics, fungistatics, coccidiostatics, hormone preparations, substances with an anabolic action, or other substances promoting growth, or improving the quality of the meat of slaughter cattle, or useful in some other way for the organism of animals.

Suitable dosage units for oral adminstration, such as dragees or tablets, preferably contain 100 to 500 mg of the active substance according to the invention, that is, 20 to 80% of a compound of the general formula I. The dosage units are produced by the combining of the active substance with, for example, solid pulverulent carriers such as lactose, saccharose, sorbitol, mannitol, starches such as potato starch, maize starch or amylopectin, also laminaria powder or citrus pulp powder, cellulose derivatives or gelatine, optionally with the addition of lubricants such as magnesium or calcium stearate, or polyethylene glycols, to form tablets or dragee cores. The last-mentioned are coated with, e.g. concentrated sugar solutions which can also contain, e.g. gum arabic, talcum and/or titanium dioxide; or with a lacquer dissolved in readily volatile organic solvents or solvent mixtures. It is also possible to add dyestuffs to these coatings, e.g. for the identification of the various doses of active substance.

In the following are described certain tests carried out to determine the anthelmintic activity of the new benzazoles of the general formula I.

Determination of the Anthelmintic Activity on Fowl Infested with Ascaridia galli.

One- to three-day old chickens were artificially infested with eggs of Ascaridia galli (ascarids). Groups each of 5 chickens were used for each test. The active substances were administered to the chickens 4 to 5 weeks after infestation, the administration being in the form of a single dose per day on 3 successive days. Infested chickens which had not been treated with the active substances were taken as a control.

Evaluation:

The number of Ascaridia galli discharged by each test group in the course of 5 days after the first administration of the active substance were determined daily, and also the number found on examination on the 5th test day in the intestines. Furthermore, the number of chickens free from worms was determined.

| Active substance | daily dose mg/kg of body weight | No. of Ascaridia galli from 5 chicks discharged during duration of test absol-ute No | in % of total No | found on dissection | No. of worm-free chickens | General condition |
|---|---|---|---|---|---|---|
| 2-Phenoxy-6-isothiocyano-1,3-benzothiazole | 750 | 108 | 100 | 0 | 5 | good |
| 2-(3'-Chlorphenoxy)-6-isothiocyano-1,3-benzthiazole | 750 | 219 | 100 | 0 | 5 | good |
| 2-(2'-Chlorophenoxy)-6-isothiocyano-1,3-benzthiazole | 750 | 61 | 100 | 0 | 5 | good |
| 2-(4'-Fluorphenoxy)-6-isothiocyano-1,3-benzthiazole | 750 | 113 | 100 | 0 | 5 | good |
| 2-(4'-Methylphenoxy)-6-isothiocyano-1,3-benzthiazole | 750 | 60 | 100 | 0 | 5 | good |
| 2-(3'-Methoxy-phenoxy)-6-isothiocyano-1,3-benzthiazole | 750 | 116 | 100 | 0 | 5 | good |
| 2-(2'-Fluorophenoxy)-6-isothiocyano-1,3-benzthiazole | 750 | 80 | 100 | 0 | 5 | good |
| 1-Methyl-2-(p-isothiocyanophenyl-thio)-benzimidazole-chlorhydrate | 750 | 182 | 100 | 0 | 5 | good |
| 2-(3'-Isothiocyanophenoxy)-1-methyl-benzimidazole-hydrochloride | 750 | 231 | 96 | 8 | 3 | good |

Tests on Mice Infested by Hymenolepsis Nana

The active substance were administered in the form of a suspension by means of a stomach probe to white mice artificially infested with Hymenolepis nana. Five animals were used per test. The active substances were administered once daily to each group of animals on three successive days. The animals were killed and dissected on the 8th day after commencement of the treatment.

After dissection of the test animals, an evaluation was made by a count of the tapeworms present in the intestines. Untreated mice which had been infested at the same time and in the same manner served as a control.

The agents were well tolerated by the mice and no resulting symtoms were observed.

| Active substances | Daily dose mg/kg of body weight | Infestation of the 5 test mice on dissection | Infestation of the control mice on dissection |
|---|---|---|---|
| 2-(m-Isothiocyano-phenylamino)-benzoxazole | 750 | 0-0-0-0-0 | 2-7-11-19-24 |
| 2-Phenoxy-6-isothiocyano-1,3-benzothiazole | 750 | 0-0-0-0-0 | 10-12-14-17-22 |
| 2-(4'-Isothiocyano-phenoxy)-6-isothiocyano-1,3-benzthiazole | 750 | 0-0-0-0-0 | 12-15-16-19-25 |
| 2-(3'-Chlorophenoxy)-6-isothiocyano-1,3-benzothiazole | 750 | 0-0-0-0-2 | 12-15-16-19-25 |
| 2-(4'-Fluorophenoxy)-6-isothiocyano-1,3-benzothiazole | 750 | 0-0-0-0-1 | 2-4-5-8-20 |
| 2-(2',3',5'-Trimethyl-phenoxy)-5-isothiocyano-1,3-benzothiazole | 750 | 0-0-0-0-0 | 0-1-2-2-4 |
| 2-(2'-Methylphenoxy)-6-isothiocyano-1,3-benzo- | 750 | 0-0-0-0-1 | 3-4-15-18-19 |

| Active substances | Daily dose mg/kg of body weight | Infestation of the 5 test mice on dissection | Infestation of the control mice on dissection |
|---|---|---|---|
| thiazole | | | |
| 2-(4'-Methylphenoxy)-6-isothiocyano-1,3-benzo-thiazole | 750 | 0-0-0-0-0 | 7-8-12-16-20 |
| 2-(2',4',5'-Trimethylphenoxy)-6-isothiocyano-1,3-benzothiazole | 750 | 0-0-0-0-2 | 4-5-6-6-11 |
| 2-(2'-Fluorophenoxy)-6-isothiocyano-1,3-benzothiazole | 750 | 0-0-0-0-0 | 2-6-7-11-16 |
| 2-(4'-Isothiocyano-phenoxy)-1,3-benzothiazole | 750 | 0-0-0-0-0 | 10-16-17-26-33 |
| (2-[-isothiocyano-phenylamino]-5-isothiocyano-benzimidazole | 750 | 0-0-0-0-0 | 11-12-12-16-16 |
| 2-[4'-Isothiocyano-phenylthio]-benzimidazole | 750 | 0-0-0-0-0 | 1-1-2-3-3 |
| 2-(3'-Isothiocyanophenoxy)-benzimidazole | 750 | 0-0-0-0-1 | +-6-6-14-16 |
| 2-(4'-Isothiocyanophenoxy)-benzimidazole | 750 | 0-0-0-0-1 | 2-6-7-11-16 |
| 2-(3'-Isothiocyanophenoxy)-1-methyl-benzimidazole-hydrochloride | 750 | 0-0-0-0-0 | 2-6-7-11-16 |
| 2-(3'-Isothiocyanophenoxy)-1-methyl-benzimidazole | 750 | 0-0-0-0-0 | 3-6-6-7-8 |
| 2-(4'-Isothiocyanophenoxy)-1-methyl-benzimidazole-hydrochloride | 750 | 0-0-0-0-0 | 11-13-16-23-32 |
| 2-(4'-Isothiocyano-phenylamino)-6-isothiocyano-benzoxazole | 750 | 0-0-0-0-0 | 4-5-7-8-18 |

Tests on Mice Infested by Oxyuris

The active substances were administered in the form of a suspension by means of a stomach probe to white mice infested with oxyuris of mice. Five animals were used for each test. The active substances were administered to each group of mice once daily on 3 successive days.

The daily dose per animal was 750 mg of active substance per kg of body weight.

The animals were killed and dissected on the 6th day after commencement of the treatment. After dissection of the animals, the evaluation was made on the basis of a count of the mice-oxyuris present in the intestines. Untreated animals which had been infested in the same manner were taken as a control.

The agents were well tolerated by the mice and no resulting symtoms were observed.

Tests on Rats Infested by Fasciola Hepatica

White laboratory rats are artificially infested with Fasciola hepatica. At the end of the prepatent time, the infestation of the rats by Fasciola hepatica (common liver fluke) was determined by means of 3 successive analyses of the excrement.

In each test, 4 infested rats are treated with the active substance, administered in the form of a suspension by stomach probe, once daily on three successive days. In the 3rd to 5th week after administration of the active substance, an excrement analysis is carried out once weekly to determine the content of eggs of the common liver fluke (Fasciola hepatica). The test animals were killed at the end of the 5th week after commencement of the test, and an examination made of the number of common liver fluke still present.

| Active substance | Daily dose mg/kg of body weight | Infestation of the five test mice | Infestation of the control animals on dissection |
|---|---|---|---|
| 2-(n-Isothiocyano-phenylamine)-benzoxazole | 750 | 0-0-0-0-0/ | 4/L1-13/L/1-15/L-18/L/1 20/L/1 |
| 2-Phenoxy-6-isothiocyano-1,3-benzthiazole | 750 | 0-0-0-0-0 | 6/L/1-8/L/1-9/L/1-11/L/1 13/L/1 |
| 2-(4'-Isothiocyano-phenylthio)-1,3-benzo-thiazole | 750 | 0-0-0-0- | 6/L/1-8/L/1-9/L/1-11/L/1 13/L/1 |
| 2-(3'-Bromophenoxy)-6-isothiocyano-1,3-benzthiazole | 566 | 0-0-0-0-0 | 10/L/1-13/L/1 |
| 2-(4'-Fluorophenoxy)-6-isothiocyano-1,3-benzo-thiazole | 750 | 0-0-0-0-0/ | 2/L/1-4/L/1-4/L/1-10/L/1 11/L/1 |
| 2-(2'-Methylphenoxy)-6-isothiocyano-1,3-benzothiazole | 750 | 0-0-0-0-0 | 8/L/1-8/L/1-14/L/1-15/L/1 20/L/1 |
| 2-(4'-Methylphenoxy)-6-isothiocyano-1,3-benzthiazole | 750 | 0-0-0-0-0 | 4/1-5-8/L/1-8/L/1-3/L/1 |
| 2-(2'-Fluorophenoxy)-6-isothiocyano-1,3-benzthiazole | 750 | 0-0-0-0-0/ | 0/L-1-3/L-15-24 |
| 2-(4'-Isothiocya-no-phenoxy)-1,3-benzthiazole | 750 | 0-0-0-0/-0 | 2-5/L/1-5/L/1-10/L/1 13/L/1 |
| 2-4'-Isothiocyanatophenoxy)-6-isothiocyano-benzimidazole | 750 | 0-0-0-0-2 | 4/L/1-5/L/1-5/L/1-6-6/L/1 |
| 2-(2'-Methyl-3'-methoxy-phenoxy)-6-isothio-cyano-1,3-benzthiazole | 750 | 0-0-0-0-0 | 5/L/1-6-6/1-7-15/L/1 |
| 2-(3'-Isothiocyanophenoxy)-1-methyl-benzimidazole-hydrochloride | 750 | 0-0-0-0-1 | 0/L-1-3/L-15-24 |

| Active substance | Daily dose in mg/kg of body weight | Excrement (?) examination, egg discharge before medication | Excrement (?) examination, egg discharge after medication | No. of common liver fluke after dissection | General condition |
|---|---|---|---|---|---|
| 2-Phenoxy-6-isothiocyano-1,3-benzothiazole | 200 | positive | negative | 0-0-0-0 | good |
| 2-(4'-Fluorophenoxy)-6-isothiocyano-1,3-benzothiazole | 200 | positive | negative | 0-0-0-0 | good |
| 2-(2'-Methylphenoxy)-6-isothiocyano-1,3-benzothiazole | 200 | positive | negative | 0-0-0-0 | good |
| 2-(2'-Fluorophenoxy-6-isothiocyano-1,3-benzothiazole | 200 | positive | negative | 0-0-0-0 | good |
| 2-[4'-Isothiocyano-phenylthio]-benzimidazole | 150 | positive | negative | 0-0-0-0 | good |
| 1-Methyl-2-(p-isothiocyanophenylthio)-benzimidazol-chlorhydrate | 200 | positive | negative | 0-0-0-0 | good |
| 2-(3'-Isothiocyanophenoxy)-benzimidazole hydrochloride | 200 | positive | negative | 0-1-0-0 | good |
| 2-(3'-Isothiocyanophenoxy)-1-methyl-benzimidazolehydrochloride | 200 | positive | negative | 0-0-0-0 | good |
| 2-(3'-Isothiocyanophenoxy)-1-methyl-benzimidazole | 200 | positive | negative | 0-0-0-0 | good |
| 2-(4'-Isothiocyanophenoxy)-1-methyl-benzimidazole | 200 | positive | negative | 0-0-0-0 | good |
| 2-(4'-Isothiocyanophenoxy)-1-methyl-benzimidazole-hydrochloride | 200 | positive | negative | 0-0-0-0 | good |
| 2-(4'-Isothiocyanophenoxy)-benzimidazole sulphuric acid salt | 150 | positive | negative | 0-0-0-0 | good |

The following examples serve to further illustrate the production processes according to the invention. Where not otherwise stated, the term 'parts' denotes parts by weight; the temperatures are expressed in degrees Centigrade.

EXAMPLE 1

6-Isothiocyano-2-Phenoxybenzothiazole

An amount of 8.46 g of thiophosgene in a sulphonating flask is stirred into 500 ml of ice water. An addition is then made dropwise, in the course of 10 minutes, of a solution of 18 g of 6-amino-2-phenoxybenzothiazole in 100 ml of dioxane as well as 10 ml of water. The suspension is further stirred overnight at room temperature. The formed precipitate is separated and washed with water; the residue is dissolved in 100 ml of methylene chloride, and the solution dried over sodium sulphate. After chromatography with methylene chloride through aluminium oxide (neutral, activity stage III), an amount of 12.5 g. of 6-isothiocyano-2-phenoxybenzothiazole, M.P. 118° to 119°C, is obtained.

EXAMPLE 2

2-(3'-Isothiocyanophenoxy)-1-Methylbenzimidazole a. An amount of 74.6 g of 3-aminophenol is heated, under nitrogen, with 24 g of 80% ground potassium hydroxide to 100°; an addition is then made at this temperature of 57 g of 2-chloro-1-methylbenzimidazole. The mixture is subsequently heated to 140° to 145° and maintained for 5 hours at this temperature, whilst the water forming is continuously distilled off. The mixture is then diluted whilst still hot with 100 ml of dimethylformamide, and poured on to 1,500 ml of water. The formed precipitate is filtered off under suction and, while still moist, boiled with 400 ml of ethanol with the addition of active charcoal. After filtration, the filtrate is diluted with 400 ml of water and the whole stirred. 2-(3'-Aminophenoxy)-1-methylbenzimidazole, M.P. 110° to 114°, precipitates out.

b. An amount of 35 g of thiophosgene, 250 ml of dioxane and 100 ml of water is placed into a sulphating flask and cooled to 0° to 5°; an addition is then made dropwise, within 30 minutes, of a solution of 61 g of 2-(3'-aminophenoxy)-1-methylbenzimidazole in 200 ml of dioxane. The mixture is stirred for 3 hours at 0° to 5°; it is afterwards further stirred for 15 hours at room temperature. After dilution with 600 ml of water, the precipitate is separated and stirred, for 7 hours at 10°, into a solution of 10 g of thiophosgene in 500 ml of acetone. The product is separated and recrystallized from acetonitrile to obtain 29.3 g of (3'-isothiocyanophenoxy)-1-methylbenzimidazolehydrochloride, M.P. 154° to 158°C.

6 Parts of this product are treated with a saturated sodium bicarbonate solution. The obtained base is taken up in chloroform. After drying and distillation of the solution, the residue, recrystallised from cyclohexane, yields 4.2 g of 2-(3'-isothiocyanophenoxy)-1-methylbenzimidazole, M.P.: 121° - 124°C.

EXAMPLE 3 (Compound - see Example 2)

An amount of 4.8 g of 2-(3'-aminophenoxy)-1-methylbenzimidazole is refluxed with 3.0 g of diethylaminothiocarbonyl chloride in 50 ml of anhydrous toluene for 4 hours. The mixture is filtered hot and the filtrate concentrated by evaporation to dryness. The residue is boiled in cyclohexane. The hot suspension is filtered off, diluted while still hot with petroleum ether, and filtration performed to obtain 2-(3'-isothiocyanantophenoxy)-1-methylbenzimidazole, M.P.: 120° to 121°C.

EXAMPLE 4

2-(4'-Isothiocyanophenoxy)-1-Methylbenzimidazole

An amount of 4.8 g of 2-(4'-aminophenoxy)-1-methylbenzimidazole is stirred with 2.3 g of bis-(trichloromethane-sulphonyl-trithiocarbonate in 25 ml of water for 24 hours at room temperature. The precipitate is separated, washed with sodium bicarbonate solution, and taken up in chloroform. After drying and distillation of the chloroform solution, the residue is boiled out with cyclohexane, filtered hot, and the filtrate diluted with petroleum ether. The 2-(4'-isothiocyanophenoxy)-1-methylbenzimidazole crystallising out melts at 59° to 61°C.

EXAMPLE 5

2-(4'-Isothiocyanophenoxy)-1,3-Dimethylbenzimidazolium-Iodide

An amount of 14.3 g of 2-(4'-isothiocyanophenoxy)-1-methylbenzimidazole is refluxed with 6.8 g of methyl iodide in 50 ml of anhydrous acetone for 21 hours. The solution is then diluted with ether, the precipitate filtered off, and the filtrate concentrated by evaporation to dryness to obtain 16 g of 2-(4'-isothiocyanophenoxy)I-1,3-dimethylbenzimidazolium iodide, M.P.: 204° to 208°C.

EXAMPLE 6 a. A solution of 83 g of p-nitroaniline in 400 ml of dioxane is added at room temperature, with stirring, to 126 g of 2-chloro-6-nitrobenzoxazole obtained from 43.3 g of 2-chlorobenzoxazole with fuming nitric acid (d. 1.52) in sulphuric acid. The solution is heated to 40°C and stirred at this temperature for a further 19 hours. The solution is diluted with 200 ml of water; it is then cooled and the precipitate separated. The suction-filter residue is dried and dissolved in 500 ml of dimethylformamide. This solution is purified, and diluted with 200 ml of ethanol. The precipitating 6-nitro-2-(4'-nitroanilino)-benzoxazole has the melting point 305° to 310°C.

b. An amount of 47 g of 6-nitro-2-(4'-nitroanilino)-benzoxazole is dissolved in 500 ml of dimethylformamide; and 7 g of palladium charcoal (5%) then added. Within 3 hours at room temperature, 18.6 ml of hydrogen is absorbed. The catalyst is then filtered off, and the filtrate concentrated in a water-jet vacuum at 70°C to dryness. The residue is afterwards dissolved with 250 ml of 2-n HCl, and the solution rendered alkaline with concentrated ammonia solution. 6-Amino-2-(4'-aminoanilino)-benzoxazole, M.P. 83° to 87°, precipitates.

c. A suspension of 17.2 g of 6-amino-2-(4'-aminoanilino)-benzoxazole in 200 ml of anhydrous chlorobenzene is saturated at room temperature with hydrogen chloride. An amount of 13.2 g of $NH_4SCN$ (ammonium thiocyanate) is subsequently added to the mixture. With a further slight introduction of hydrogen chloride, the reaction mixture is refluxed, with stirring, for 6 hours. After cooling, the crystallisate is separated and recrystallised from methyl ethyl ketone. The obtained 6-isothiocyano-2-(4'-isothiocyanophenylamino)-benzoxazole has the melting point 233° to 237°C.

EXAMPLE 7

2-(4'-Fluorophenoxy)-6-isothiocyanobenzothiazole

An amount of 20 g of phosgene is introduced, with ice cooling and with the exclusion of atmospheric moisture, into 100 ml of o-dichlorobenzene; an addition is then made at 0° of 13 parts of 2-(4'-fluorophenoxy)-6-aminobenzothiazole. The reaction mixture is stirred overnight at room temperature; the temperature is then raised, with a slight introduction of phosgene, within 45 minutes to 90°. The flow of phosgene is thereupon stopped, and stirring at 125° – 130° continued until the evolution of gas has finished (after ca. 2 hours). After slow cooling to room temperature, 3.75 g of phosphorus pentasulphide is added; stirring with refluxing is subsequently carried out for 14 hours, and the solution filtered off whilst still hot. The filtrate is concentrated by evaporation, and the residue chromatographed through aluminium oxide with methylene chloride as the eluant. The obtained 2-(4'-fluorophenoxy)-6-isothiocyanobenzothiazole has the M.P. 124° – 126°.

EXAMPLE 8

2-(2'-Fluorophenoxy)-6-isothiocyanobenzothiazole

An amount of 17 g of ammonium rhodanide is dissolved in 200 ml of absolute acetone; an addition is then made to the solution, with stirring, of 31 g of benzoyl chloride. The reaction mixture is allowed to boil with refluxing for 5 minutes; a solution is then added of 57 g of 2-(2'-fluorophenoxy)-6-aminobenzothiazole (obtained from 2-(2'-fluorophenoxy)-6-nitrobenzothiazole by catalytic hydrogenation, cp. Example 6) in 400 ml of acetone. Stirring is continued for 2 minutes at the boiling temperature, and the mixture then poured, with stirring, into 5000 ml of ice water. Filtration is performed, the filter residue washed with water, and suspended in 350 ml of 10% sodium hydroxide solution. The suspension is quickly brought to boiling temperature and allowed to boil for a further 2 minutes. Cooling is then rapidly carried out in an ice bath; the suspension is neutralised with 2-n hydrochloric acid, and the pH-value adjusted with 2-n ammonia to 8. Filtration is again performed, the filter residue washed wth water until neutral, and dried at 80° in vacuo. The finely powdered material is suspended in 500 ml of anhydrous chlorobenzene and refluxed for 14 hours. After the solvent has been evaporated off, the residue is chromatographed through aluminium oxide with methylene chloride as the eluant. The obtained 2-(2'-fluorophenoxy)-6-isothiocyanobenzothiazole melts at 115° – 117°.

EXAMPLE 9

2-(4'-Isothiocyanophenylthio)-benzothiazole

Hydrogen chloride is introduced for 90 minutes, with cooling, into a mixture of 12.9 g of 2-(4'-aminophenylthio)-benzothiazole (obtained from 2-(4'-nitrophenylthio)-benzothiazole by catalytic hydrogenation, see Example 6) and 15.4 g of bis-(diethyl)-thiocarbamoyl-disulphide in 250 ml of anhydrous chlorobenzene. Stirring is afterwards carried out for 4½ hours with refluxing, animal charcoal is added and filtration performed hot. The filtrate is concentrated by evaporation, and chromatographed through aluminium oxide with methylene chloride as the eluant. 2-(4'-Isothiocyanophenylthio)-benzothiazole is obtained, which melts at 84.5° – 86°.

EXAMPLE 10

2-(4'-Methylphenoxy)-6-isothiocyanobenzothiazole

Additions are made dropwise, at −10° to −15°, firstly of 31 ml of triethylamine and then of 4.3 ml of carbon disulphide to 18.4 g of 2-(4'-methylphenoxy)-6-aminobenzothiazole in 360 ml of absolute diethyl ether. Stirring is continued for ca. 12 hours at room temperature; the mixture is cooled to 0°, and an addition made at this temperature, within 30 minutes, of 6.7 ml of phosphorus oxychloride in 80 ml of absolute diethyl ether. After 10 hours' stirring at room temperature, filtration is performed; the filter residue is washed firstly with diethyl ether and then with water and dried, the product is afterwards chromatographed through aluminium oxide, with methylene chloride as the eluant, to obtain 2-(4'-methylphenoxy)-6-isothiocyanobenzothiazole, M.P. 121° – 123°.

The active substances listed in the following tables are obtained by the procedures described in the preceding examples.

| Compounds: | Melting point in °C |
|---|---|
| 2-phenoxy-6-isothiocyano-1,3-benzothiazole | 118 – 119 |
| 2-(3'-chlorophenoxy)-6-isothiocyano-1,3-benzothiazole | 102 – 103 |
| 2-(4'-chlorophenoxy)-6-isothiocyano-1,3-benzothiazole | 110 – 112 |
| 2-(2'-chlorophenoxy)-6-isothiocyano-1,3-benzothiazole | 123 – 125 |
| 2-(3',4'-dichlorophenoxy)-6-isothiocyano-1,3-benzothiazole | 140 – 142 |
| 2-(3'-bromophenoxy)-6-isothiocyano-1,3-benzothiazole | 109 – 111 |
| 2-(4'-bromophenoxy)-6-isothiocyano-1,3-benzothiazole | 111 – 113 |
| 2-(4'-iodophenoxy)-6-isothiocyano-1,3-benzothiazole | 105 – 107 |
| 2(2'-bromophenoxy)-6-isothiocyano-1,3-benzothiazole | 123 – 125 |
| 2-(3'-trifluoromethylphenoxy)-6-isothiocyano-1,3-benzothiazole | 80 – 82 |
| 2-(2'-methyl-4'-chlorophenoxy)-6-isothiocyano-1,3-benzothiazole | 101 – 103 |
| 2-(3'-methylphenoxy)-6-isothiocyano-1,3-benzothiazole | 76.5 – 77.5 |
| 2-(2'-methylphenoxy)-6-isothiocyano-1,3-benzothiazole | 115 – 117 |
| 2-(2',5'-dimethylphenoxy)-6-isothiocyano-1,3-benzothiazole | 78 – 80 |
| 2-(2',4'-dimethylphenoxy)-6-isothiocyano-1,3-benzothiazole | 116 – 118 |
| 2-(3',5'-dimethylphenoxy)-6-isothiocyano-1,3-benzothiazole | 100 – 101 |
| 2-(2',3',5'-trimethylphenoxy)-6-isothiocyano-1,3-benzothiazole | 99 – 100 |
| 2-(2',4',5'-trimethylphenoxy-6-isothiocyano-1,3-benzothiazole | 83 – 85 |
| 2-(2'-methyl-3'-methoxyphenoxy)-6-isothiocyano-1,3-benzothiazole | 118 – 120 |
| 2-(3'-methoxy-4'-methylphenoxy)-6-isothiocyano-1,3-benzothiazole | 136 – 137 |
| 2-(2'-methoxy-4'-methylphenoxy)-6-isothiocyano-1,3-benzothiazole | 134.5 – 136 |
| 2-(4'-methoxyphenoxy)-6-isothiocyano-1,3-benzothiazole | 95 – 96.5 |
| 2-(3'-methoxyphenoxy)-6-isothiocyano-1,3-benzothiazole | 75 – 77 |
| 2-(2'-methoxyphenoxy)-6-isothiocyano-1,3-benzothiazole | 104 – 105 |
| 2-(2'-naphthoxy)-6-isothiocyano-1,3-benzothiazole | 153 – 155 |
| 2-(4'-phenylphenoxy)-6-isothiocyano-1,3-benzothiazole | 140 – 141 |
| 2-(2'-chloro-4'-phenylphenoxy)-6-isocyano-1,3-benzothiazole | 108 – 112 |
| 2-(4'-isothiocyanophenoxy)-1,3-benzothiazole | 82 – 85 |
| 2-(4'-isothiocyanophenoxy)-6-nitro-1,3-benzothiazole | 174 – 176 |
| 2-(3'-isothiocyanophenoxy)-6-isothiocyano-1,3-benzothiazole | 129 – 131 |
| 2-(4'-isothiocyanophenoxy)-6-isothiocyano-1,3-benzothiazole | 125 – 127 |
| 2-phenylthio-6-isothiocyano-1,3-benzothiazole | 126 – 128 |
| 2-(4'-chlorophenylthio)-6-isothiocyano-1,3-benzothiazole | 138 – 140 |
| 2-(4'-bromophenylthio)-6-isothiocyano-1,3-benzothiazole | 141 – 143 |
| 2-(4'-methylphenylthio)-6-isothiocyano-1,3-benzothiazole | 123 – 125 |
| 2-(4'-tert.butylphenylthio)-6-isothiocyano-1,3-benzothiazole | 127 – 129 |
| 2-(4'-isothiocyanatophenylthio)-6-nitro-1,3-benzothiazole | 155 – 157 |
| 2-(phenylmethylamino)-6-isothiocyano-benzothiazole | 139 – 141 |
| 6-isothiocyano-2-phenylamino-benzothiazole | 195 – 199 |
| 2-(4'-methylphenylamino)-6-isothiocyanobenzothiazole | 202 – 204 |
| 2-(3'-isothiocyanophenylamino)-6-isothiocyanobenzothiazole | 199 – 202 |
| 2-benzyloxy-6-isothiocyano-benzothiazole | 98 – 99 |
| 2-(N-benzyl-N-methylamino)-6-isothiocyanobenzothiazole | 113 – 115 |
| 2-(4-isothiocyanobenzylthio)-benzothiazole | 89 – 91 |
| 2-(3'-phenylpropoxy)-6-isothiocyanobenzothiazole | 58 – 61 |
| 2-(3'-isothiocyanophenoxy)-benzimidazole | 203 – 204 |
| 2-(3'-isothiocyanophenoxy)-benzimidazole hydrochloride | 200 – 203 |
| 2-(4'-isothiocyanophenoxy)-benzimidazole | 206 – 210 |
| 2-(3'-isothiocyanophenoxy)-1-methyl-benzimidazole | 121 – 124 |
| 2-(4'-isothiocyanophenoxy)-benzimidazole sulphuric acid salt | 207 – 208 |
| 2-(4'-isothiocyanophenoxy)-1-methyl-benzimidazole-hydrochloride | 150 – 153 |
| 2-(4'-isothiocyanophenoxy)-3-methyl-(5 or 6)-nitrobenzimidazole | 218 |
| 2-(3-isothiocyanophenoxy)-(5 or 6)-nitrobenzimidazole | 175 |
| 2-[4'-isothiocyanophenylthio]-benzimidazole | 253 – 257 |
| 1-methyl-2-(4'-isothiocyanophenylthio)-5(6)-nitrobenzimidazole | 162 |
| 1-methyl-2-(p-isothiocyanophenylthio)-benzimidazole-chlorohydrate | 200 – 202 |
| 2-(4'-isothiocyanobenzylthio)-benzimidazole | 174 – 178 |
| 2-(p-isothiocyanophenylamino)-5-chlorobenzimidazole | 245 – 247 |
| 2-(4'-isothiocyanatophenoxy)-5-isothiocyanobenzimidazole | 189 – 192 |
| 2-(m-isothiocyanophenylamino)-5-isothiocyanobenzoxazole | 185 – 187 |
| 2-[isothiocyanophenylamino]-5-isothiocyanobenzimidazole | 230 |
| 2-(4'-methoxyphenylamino)-5-isothiocyanobenzimidazole | 136 – 140 |
| 2-(4'-chlorophenylamino)-5-isothiocyanobenzimidazole hydrochloride | 225 – 227 |
| 2-(4'-methylbenzylthio)-5-isothiocyanobenzimidazole | 174 – 176 |
| 2-(4'-isothiocyanophenylthio)-benzoxazole | 67 – 71 |
| 2-(4'-isothiocyanophenylamino)-benzoxazole | 242 – 244 |
| 2-(m-isothiocyanophenylamino)-benzoxazole | 177 – 179 |
| 2-(m-isothiocyanophenylamino)-6-methylbenzoxazole | 191 – 193 |
| 2-(phenylmethylamino)-6-isothiocyanobenzoxazole | 81 – 83 |
| 2-(4'-methoxyphenylamino)-6-isothiocyanobenzoxazole | 234 – 236 |
| 2-(4'-isothiocyanophenoxy)-benzoxazole | 105 – 109 |
| 2-(4'-chlorophenylthio)-6-isothiocyanobenzoxazole | 98 – 104 |
| 2-(4'-isothiocyanophenylthio)-6-nitrobenzoxazole | 154 – 156 |
| 2-(N-benzyl-N-methylamino)-6-isothiocyanobenzoxazole | 77 – 79 |
| 2-(4'-chlorobenzylthio)-6-isothiocyanobenzoxazole | 121 – 123 |
| 2-(4'-isothiocyanobenzylthio)-benzoxazole |  |

We claim:

1. An isothiocyano-benzoxazole compound of the formula wherein one of $R_2$ and $R_5$ is isothiocyano and the other is selected from the group consisting of hydrogen, isothiocyano, methyl, methoxy, chlorine and nitro; Y is oxygen, sulphur or $$-\underset{R}{\underset{|}{N}}-$$

in which R is hydrogen or methyl; and $n$ is 0 or 1.

2. The compound according to claim 1 which is 2-(m-isothiocyano-phenylamino)-benzoxazole.

3. The compound according to claim 1 which is 2-(4'-isothiocyano-phenylamino)-6-isothiocyanobenzoxazole.

\* \* \* \* \*